(12) United States Patent
DiLeva

(10) Patent No.: US 7,691,419 B2
(45) Date of Patent: Apr. 6, 2010

(54) COMPOSITIONS AND METHODS FOR TREATING SKIN CONDITIONS IN MAMMALS

(76) Inventor: Rose Marie DiLeva, 20 Park La., Glenn Mills, PA (US) 19342

( * ) Notice: Subject to any disclaimer, the term of this patent is extended or adjusted under 35 U.S.C. 154(b) by 0 days.

(21) Appl. No.: 11/961,333

(22) Filed: Dec. 20, 2007

(65) Prior Publication Data

US 2009/0162304 A1 Jun. 25, 2009

(51) Int. Cl.
| | |
|---|---|
| *A61K 36/61* | (2006.01) |
| *A61K 36/886* | (2006.01) |
| *A61K 36/53* | (2006.01) |
| *A61K 36/00* | (2006.01) |
| *A61K 36/87* | (2006.01) |
| *A61K 31/355* | (2006.01) |

(52) U.S. Cl. ............... 424/725; 424/742; 424/776; 424/766; 424/744; 514/458

(58) Field of Classification Search ............ None
See application file for complete search history.

(56) References Cited

U.S. PATENT DOCUMENTS

| | | | | |
|---|---|---|---|---|
| 4,784,842 | A | * | 11/1988 | London et al. ............ 424/45 |
| 6,063,406 | A | * | 5/2000 | Hornack .................. 424/678 |
| 6,440,437 | B1 | | 8/2002 | Krzysik et al. |
| 6,495,148 | B1 | | 12/2002 | Abbiati |
| 6,576,269 | B1 | | 6/2003 | Korneyev |
| 6,579,543 | B1 | | 6/2003 | McClung |
| 7,226,627 | B1 | * | 6/2007 | Eckert et al. ............ 424/766 |
| 2003/0091618 | A1 | * | 5/2003 | Seth et al. .............. 424/443 |
| 2004/0234628 | A1 | * | 11/2004 | Kearns et al. ........... 424/736 |
| 2005/0152993 | A1 | * | 7/2005 | De Oliveira ............ 424/669 |
| 2005/0222543 | A1 | * | 10/2005 | Shao .................... 604/292 |
| 2006/0172022 | A1 | * | 8/2006 | Szanzer ................. 424/757 |
| 2007/0166241 | A1 | * | 7/2007 | Baker ................... 424/47 |
| 2007/0207115 | A1 | * | 9/2007 | Liegeois ................. 424/74 |

FOREIGN PATENT DOCUMENTS

| | | | | |
|---|---|---|---|---|
| CN | 1433753 | A | * | 8/2003 |
| KR | 2006092333 | A | * | 8/2005 |

* cited by examiner

*Primary Examiner*—Michele Flood
*Assistant Examiner*—Qiuwen Mi
(74) *Attorney, Agent, or Firm*—Fox Rothschild LLP; Gerard P. Norton; Roman Fayerberg

(57) ABSTRACT

A topical composition for treating skin diseases is provided. The composition comprises *calendula*, tea tree oil, *eucalyptus* oil, grape seed oil, and *Aloe vera*. In some embodiment, the composition may also include beeswax, vegetable oil, vitamin E, rosemary oil, or shea butter or combinations thereof to further enhance its beneficial effects. In some embodiments, the composition may also include herbs. Kits and methods for treatment of skin diseases are also disclosed.

4 Claims, No Drawings

COMPOSITIONS AND METHODS FOR TREATING SKIN CONDITIONS IN MAMMALS

FIELD OF THE INVENTION

This invention relates to a composition for treatment of skin diseases.

BACKGROUND OF THE INVENTION

The largest organ of our bodies, the skin is what separates us from the outside world. It holds body fluids in, preventing dehydration, and keeps harmful microbes out—without it mammals would succumb to infection. Unfortunately, it is susceptible to a variety of diseases. Skin diseases include rashes, blisters, acne, fungal infections such as athlete's foot, ringworm, burns, insect bites, microbial infections, sunburn, scabies, scrapes and cuts, among many others. Over the years, various compositions have been developed to treat these diseases. Most of these compositions, however, are only suitable for treatment of a single disease.

Accordingly, there is still a need for a composition that may be utilized to successfully treat various diseases.

SUMMARY OF THE INVENTION

In one aspect, a topical composition for treating skin diseases is provided. The composition comprises *calendula*, tea tree oil, *eucalyptus* oil, grape seed oil, and *Aloe vera*. The composition may also include beeswax, vegetable oil, Vitamin E, Rosemary oil, or Shea butter.

The composition may be presented in the form selected from the group consisting of sticks, bars, gels, lotions, pastes, balms, creams and ointments, body washes, face washes, rinses, sprays and oral tinctures.

The composition may further comprise at least one secondary active agent. In one embodiment, the secondary active ingredient comprises herbs. Alternatively, the secondary active ingredient may be selected from the group consisting of vitamins, antimicrobial agents, anti-inflammatory agents, non-steroidal cosmetic soothing agents, skin lightening agents, anti-wrinkle agents, anti-itching agents, antioxidants, fragrances, conditioners, and combinations thereof.

In another aspect, a kit for treating skin diseases is provided. It comprises a composition as described above and a set of instructions. In some embodiments, it may also include an applicator for applying the composition to the skin.

In yet another aspect, a method of treating a skin affected by a skin disease in a mammal is provided. Such method comprises administering an effective amount of a composition as described above to the affected area.

DETAILED DESCRIPTION

Applicant has unexpectedly discovered that a composition comprising *calendula*, tea tree oil, *eucalyptus* oil, grape seed oil, and *Aloe vera* is effective in treatment of various skin diseases in mammals. Addition of beeswax, vegetable oil, Vitamin E, Rosemary oil, herbs, Shea butter, or combinations thereof to such composition may further enhance its beneficial effects.

Main Ingredients:

*Calendula*: *Calendula* is a genus of about 12-20 species of annual or perennial herbaceous plants in the daisy family Asteraceae. *Calendula* contains chemicals that have been shown in animal studies to speed up wound healing by several actions that include increasing blood flow to the affected area and promoting the production of collagen proteins. *Calendula* also possesses antiseptic and anti-inflammatory effects due to its flavonoid content. It has been widely used on the skin to treat minor wounds, skin infections and inflammations, burns, bee stings, sunburn, warts, and cancer, surgical incisions, skin irritations, chapped lips, cracked skin among others. Aside from allergic reactions, few severe reactions to *calendula* have been found in published reports.

Although *Calendula* oil is readily available from commercial sources described below, it may also be made from vegetable, soy or other oils in which 60-80 grams of dried *calendula* herb is placed in 1 gallon of the oil and allowed to sit in the sun for a natural extraction process for a period of at least 3 months. The mixture may be agitated 2 to 7 times a week. This process can be accelerated if demand surpasses supply, using heat extraction, by heating the mixture over a slow heat from 30 minutes to a period of hours depending upon the volume desired.

Tea Tree Oil: Tea tree oil or *melaleuca* oil is an essential oil obtained by steam distillation of the leaves of the *Melaleuca alternifolia* tree. The oil is believed to have beneficial cosmetic and medical properties. It is believed to possess anesthetic, anti-bacterial, antiseptic and anti-fungal properties. As such, it is valuable as a first aid treatment for a range of complaints. It makes an excellent topical oil to prevent infections and accelerate the healing of small cuts and grazes, and also bruises. It removes the itch and irritation caused by insect bites. Tea tree oil can also be applied to areas of severe sunburn to provide relief and prevent blistering.

*Eucalyptus* oil: *Eucalyptus* oils are obtained by distillation of the leaves of *Eucalyptus*. The *Eucalyptus* oils are used for medicinal, perfumery and industrial purposes. Medicinal oils are characterized by a high eucalyptol content which has been demonstrated to reduce inflammation and pain.

Grape Seed Oil: Grape seed oil is a vegetable oil pressed from the seeds of various varieties of *Vitis vinifera* grapes. It used primarily for it's high proanthocyanidin content which is bioflavonoid with a demonstrated anti-oxidant properties. Proanthocyanidins are also considered helpful in improving and preserving the elasticity of skin by stabilizing collagen and elastin. Accordingly, the grape seed oil is commonly used for treatment of damaged and stressed tissues. It can help skin retain the normal structure of epithelium cells and nerve cells via supporting the cell membranes.

*Aloe Vera*: Transparent gel from the pulp of the meaty leaves of *Aloe vera* has been used topically for thousands of years to treat wounds, skin infections, burns, and numerous other dermatologic conditions. Many of *Aloe vera's* beneficial properties may be attributed to polysaccharides such as glucomannan and acemannan. In some embodiments, suitable *Aloe vera* may be used either in water or oil-based liquid forms. In other embodiments, water may be added to oil-based *aloe* liquid to adjust the oiliness of the liquid.

Beeswax: Beeswax is a product from a bee hive, specifically the hive of any species of honey bee (the genus *Apis*). It is purified to remove impurities using well known techniques to produce the commercial product.

Vegetable oil: Vegetable oils are substances derived from plants that are composed of triglycerides. The oils are extracted from vegetables by chemical extraction or physical extraction methods and purified. Examples of vegetable oils include, but are not limited, to soybean oil, corn oil, coconut oil, carrot oil, sunflower oil, rapeseed oil, peanut oil, castor oil, pumpkin seed oil, cottonseed oil, palm oil, sesame oil, or combinations thereof.

Shea butter: Shea Butter is a natural butter extracted from the nuts of the Shea tree by traditional techniques, i.e. using water as an extraction solvent, or using other solvents such as, for example, ethanol or hexane. Shea butter is known for its properties as a moisturizer and emollient and as an anti-inflammatory agent.

Vitamin E: The term Vitamin E, Tocopherol, refers to a series of organic compounds that include methylated phenols. Here, the term Vitamin E also includes the various derivatives of these compounds. Vitamin E is a fat-soluble antioxidant. It is also known to promote healing of skin wounds.

Rosemary Oil: Rosemary essential oil may be extracted from Rosemary herb by steam distillation. The main chemical components of rosemary oil are a-pinene, borneol, b-pinene, camphor, bornyl acetate, camphene, 1,8-cineole and limonene. Rosemary oil is used for its many therapeutic properties such as analgesic, antidepressant, astringent, carminative, cephalic, cholagogue, cordial, digestive, diuretic, emmenagogue, hepatic, hypertensive, nervine, rubefacient, stimulant, sudorific and tonic propterties.

The ingredients described above are readily available commercially in various forms from, for example, The Herbarie at Stoney Hill Farm, Inc. of Prosperity, S.C., or HERBSMD.COM of Torrance, Calif., among many other sources.

A person skilled in the art should be able to select the appropriate amount of ingredients on the basis of his general knowledge, taking into account on the one hand the nature of the constituents used, and on the other hand the intended use of the composition. For example, adjustments in the proportions of Tea Tree Oil and *Eucalyptus* Oil may be decreased, for example, in conditions where the composition is used as an ear ointment, so as not to cause a tingling or burning sensation in severe cases of otits externa, otitis media or otitis interna (mild to severe ear infection/inflammation), where serious ulceration of the area may exist.

By way of non-limiting example, a composition may generally include from between about 20% to about 65% weight per volume of *Calendula* Oil, from about 0.01% to about 5% weight per volume of Tea Tree Oil, from about 0.01% to about 15% weight per volume of *Eucalyptus* Oil, from about 0.01% to about 15% weight per volume of Grape Seed Oil, and from about 0.01% to about 20% weight per volume of *Aloe Vera* Oil. In some embodiments, the composition may also include from about 0.01 to 8% weight per volume of Vitamin E, from about 0.00 to 20% weight per volume of Shea Butter, from about 0.01% to about 2% of weight per volume Rosemary oil, from about 0.00% to about 40% weight per volume of beeswax, from about 15% to about 55% weight per volume of vegetable oil, from about 0.00% to 40% weight per volume of herbs, or combinations thereof. Some embodiments may also include white vinegar or gentian violet.

Topical Compositions:

In one embodiment of the present invention, the composition may be applied on the surface of the affected skin area in adequate quantity and in the manner conventional in the relevant field. The topical composition may be in a solid, semi-solid, or liquid form. Suitable solid topical compositions include, for example, sticks or bars similar to deodorant sticks. Suitable semi-solid mixtures topical compositions may include, for example, gels, lotions, pastes, balms, creams and ointments. Suitable liquid topical compositions include, for example, body or face washes, rinses, and sprays. Such topical compositions are useful for treating skin diseases which include, but are not limited to, rashes, blisters, acne, fungal infections, bacterial infections, burns, insect bites, microbial infections, sunburn, scabies, scrapes, cuts and combinations thereof.

A person skilled in the art can select both the appropriate presentation form and the method for preparing it on the basis of his general knowledge, taking into account on the one hand the nature of the constituents used, and on the other hand the intended use of the composition. The compositions may be prepared by any method known and practiced in the art. For example, U.S. Pat. Nos. 4,246,285; 4,847,068; 6,927,205; 5,824,323; 5,143,940; 6,030,931; and 7,186,416, which are incorporated herein by reference, disclose various skin care compositions in the form of lotions, creams, solutions, gels, foams and solids. In addition, various solid formulations of gel stick compositions are disclosed, for example, in U.S. Pat. Nos. 4,518,582; 4,719,102; 4,722,835, incorporated herein by reference.

For example, if the composition is used as a skin moisturizer it may preferably, be of an ointment consistency. If the composition is used as a lip balm the viscosity of the composition may preferably be increased to make a firmer product. The changes in viscosity of the composition may be achieved, for example, by adjusting the amount of beeswax among other methods.

The topical compositions may be formulated with liquid or solid emollients, solvents, thickeners, or humectants. Emollients include, but are not limited to, stearyl alcohol, mink oil, cetyl alcohol, oleyl alcohol, isopropyl laurate, polyethylene glycol, olive oil, petroleum jelly, palmitic acid, oleic acid, and myristyl myristate. Emollients may also include natural butters extracted from various plants, trees, roots, or seeds. Examples of such butters include, but are not limited to, shea butter, cocoa butter, avocado butter, *aloe* butter, coffee butter, mango butter, or combination thereof.

Suitable solvents include, without limitation, ethyl alcohol, isopropanol, acetone, diethylene glycol, ethylene glycol, dimethyl sulfoxide, and dimethyl formamide.

Suitable humectants include, but are not limited to, acetyl arginine, algae extract, *aloe* barbadensis leaf extract, 2,3-butanediol, chitosan lauroyl glycinate, diglycereth-7 malate, diglycerin, diglycol guanidine succinate, erythritol, fructose, glucose, glycerin, honey, hydrolyzed wheat protein/polyethylene glycol-20 acetate copolymer, hydroxypropyltrimonium hyaluronate, inositol, lactitol, maltitol, maltose, mannitol, mannose, methoxy polyethylene glycol, myristamidobutyl guanidine acetate, polyglyceryl sorbitol, potassium pyrollidone carboxylic acid (PCA), propylene glycol, sodium pyrollidone carboxylic acid (PCA), sorbitol, and sucrose. Other humectants may be used for yet additional embodiments of this invention, as will be appreciated by those skilled in the art.

Suitable thickeners include, but are not limited to, polysaccharides, in particular xantham gum, guar-guar, agar-agar, alginates, carboxymethylcellulose, relatively high molecular weight polyethylene glycol mono- and diesters of fatty acids, polyacrylates, polyvinyl alcohol and polyvinylpyrrolidone, surfactants such as, for example, ethoxylated fatty acid glycerides, esters of fatty acids with polyols such as, for example, pentaerythritol or trimethylpropane, fatty alcohol ethoxylates or alkyl oligoglucosides, and electrolytes, such as sodium chloride and ammonium chloride.

The composition may further comprise one or more penetrants, compounds facilitating penetration of active ingredients into the skin of a patient. Non-limiting examples of suitable penetrants include isopropanol, polyoxyethylene ethers, terpenes, cis-fatty acids (oleic acid, palmitoleic acid), acetone, laurocapram dimethyl sulfoxide, 2-pyrrolidone, oleyl alcohol, glyceryl-3-stearate, cholesterol, myristic acid isopropyl ester, and propylene glycol.

Additionally, the compositions may include surfactants or emulsifiers for forming emulsions. Either a water-in-oil or oil-in-water emulsion may be formulated. Examples of suitable emulsifiers include, but are not limited to, stearic acid, cetyl alcohol, PEG-100, stearate and glyceryl stearate, cetearyl glucoside, polysorbate 20, methylcellulose, sodium carboxymethylcellulose, glycerin, bentonite, ceteareth-20, cetyl alcohol, cetearyl alcohol, lanolin alcohol, riconyl alcohol, self-emulsifying wax (e.g., Lipowax P), cetyl palmitate, stearyl alcohol, lecithin, hydrogenated lecithin, steareth-2, steareth-20, and polyglyceryl-2 stearate.

In some formulation, such as in aerosol form, the composition may also include a propellant. Preferably, hydrofluoroalkanes (HFA) such as either HFA 134a (1,1,1,2,-tetrafluoroethane) or HFA 227 (1,1,1,2,3,3,3-heptafluoropropane) or combinations of the two, may be used since they are widely used in medical applications. Other suitable propellants include, but are not limited to, mixtures of volatile hydrocarbons, typically propane, n-butane and isobutane, dimethyl ether (DME), methylethyl ether, nitrous oxide, and carbon dioxide.

Those skilled in the art will readily appreciate that emollients, solvents, thickeners, humectants, penetrants, surfactants or emulsifiers, and propellants, other than those listed may also be employed.

Oral Compositions:

The compositions may also be administered orally either in solid or a liquid form. For oral administration, the compositions may be presented in the form of tablets, lozenges, pills, capsules, elixirs, powders, lyophilized powders, solutions, granules, suspensions, emulsions, syrups, and tinctures. Conventionally known methods may be used to prepare the composition in different forms.

Solid forms for oral administration may contain binders acceptable in human and veterinary pharmaceutical practice, sweeteners, disintegrating agents, diluents, flavourings, coating agents, preservatives, lubricants and/or time delay agents. Suitable binders include, but are not limited to gum acacia, gelatine, corn starch, gum tragacanth, sodium alginate, carboxymethylcellulose or polyethylene glycol. Suitable sweeteners include, but not limited to, sucrose, lactose, glucose, aspartame or saccharine. Suitable disintegrating agents include, but are not limited to, corn starch, methylcellulose, polyvinylpyrrolidone, guar gum, xanthan gum, bentonite, alginic acid or agar. Suitable diluents include, but are not limited to, lactose, sorbitol, mannitol, dextrose, kaolin, cellulose, calcium carbonate, calcium silicate or dicalcium phosphate. Suitable flavouring agents include, but are not limited to, peppermint oil, oil of wintergreen, cherry, orange or raspberry flavouring. Suitable coating agents include, but are not limited to, polymers or copolymers of acrylic acid and/or methacrylic acid and/or their esters, waxes, fatty alcohols, zein, shellac or gluten. Suitable preservatives include, but are not limited to, sodium benzoate, vitamin E, alpha-tocopherol, ascorbic acid, methyl paraben, propyl paraben or sodium bisulphite. Suitable lubricants include, but are not limited to, magnesium stearate, stearic acid, sodium oleate, sodium chloride or talc. Suitable time delay agents include glyceryl monostearate or glyceryl disteaae.

Liquid forms for oral administration may contain, in addition to the above agents, a liquid carrier. Suitable liquid carriers include, but are not limited to, water, oils such as olive oil, peanut oil, sesame oil, sunflower oil, safflower oil, arachis oil, coconut oil, liquid paraffin, ethylene glycol, propylene glycol, polyethylene glycol, ethanol, propanol, isopropanol, glycerol, fatty alcohols, triglycerides or mixtures thereof.

In one preferred embodiment, the composition is in the tincture form. Tinctures are herbal extracts. They may be prepared by using solvents to extract oils from herbs by either percolation or maceration techniques. Suitable solvents may include, but are not limited to, water, glycerin, propylene glycol, alcohol, vegetable oil, mineral oil, or combinations thereof. Processes for preparing tinctures are well known in the art and are disclosed, for example, in U.S. Pat. No. 4,952, 603 ElFeraly, et al., and U.S. Pat. Nos. 6,555,074 and 6,656, 437 to Sweet, which are incorporated herein in their entirety. Furthermore, tinctures are available commercially from companies indicated above.

Secondary Active Ingredients:

In some embodiments, in addition to the ingredients disclosed above, secondary active agents may be included into the present compositions. In some embodiments, such secondary active ingredient may include herbs in concentrations of between about 0.01% and about 40% weight per volume.

Examples of herbs include, but are not limited to Chinese herbs and other herbs such as Althea officinalis; Bei xi xin; Ashwagandha; Bei xie; Ai Pian; Bei zi cao; An nan zi; Bi xie; An xi Xiang; Bian dou; Ba dou; Bian xu; Ba dou rou; Bie jia; Ba ji; Cang er cao; Ba ji tian; Cang er zi; Ba jiao wu tong; Cang zhu; Bai ai; Cao guo; Bai bu; Cao long dan; Bai guo; Cao wu; Bai he; Chai hu; Bai ji; Chan tui; Bai ji li; Chang shan; Bai jue zi; Chen pi; Bai ju hua; Chong cao; Bai long gu; Chi zhu; Bai mao gen; Chuan bei mu; Bai qian; Chuan duan; Bai Shao; Chuan fu zi; Bai shao yao; Chuan gao ben; Bai shen; Chuan hong hua; Bai tou weng; Chuan huang bai; Bai wei gen; Chuan lian; Bai xian pi; Chuan lian zi; Bai zhi; Chuan mu tong; Bai zu; Chuan yu jin; Ban bian lian; Chuan zu; Ban la gen; Chuan xiong; Ban mao; Chun hua; Ban xia; Chun pi; Ban zhi lian; Cun dong; Bei he shi; Cordyceps sinensis; Da bei mu; Bei lian qiao; Da chong zuang juan; Bei qi; Da huang; Bei wu wei zi; Da ji; Da ma ren; Fei zi; Da sha shen; Fen dan pi; Da suan; Fang fang; Da zao; Fu hai she; Dan cao; Fu hua; Dan pi; Fu ling; Dan qin; Fu ling pi; Dan sha; Fu pen zi; Dan shen; Fu she; Dang gui shen; Fu xiao mai; Dang gui tou; Fu zi; Dang gui tou; Gan cao; Dang gui wei; Gan di huang; Dang gui; Gan di long; Dang shen; Gan ge gen; Di bie chong; Gan gen; Di ding; Gan jiang Di gu pi; Gan ju hua Di long Gan qi; Ding feng cao Gan shi Dong chong cao Gao ben Dong chong xia cao Gao li shen Dong gua ren Ge gen Dong hua Ge jie Du huo Gou qi zi; Dou chi Gua di; Du zhong Gua lou shi Dong zhu Guan gui; E guan shi Guan huang bai; E jiao Guan mu tong; E zhu Guang yu ji; Er cha Guang zhi mu; Er chou Giu ban Er hua-Gui ban jiao Fa ban xia Hai er shen Fan xie ye; Han; Fang dang Hang ju hua Fang feng He shou wu; Fang ji; Hei xuan shen Fang ling kuai Hong hua Fei zhi mu; Hong shen Fen dan pi; Hong si xian Feng fang Hou jiang Feng guo Hou po; Fo shou hua Hu gu; Hui huang lian Lian ren Hua shi dan Lian rou Huai hua Lian shi Huai mi; Lian ren Huang bo; Lian xu; Huang dan Lian xin Huang lian Ling ci shi Huang qi Ling xian gen Huang qin-Ling yang jiao Huang yao zi-Liu huang Huo ma ren Liu ji nu; Ji cai Liu ji nu cao Ji nei ji; Long dan Ji lin shen Long dan cao Ji zhiun pi; Long gu; Juan bei mu; Long hu cao Jiang huang Long yan rou Jiang ban xia Lou ren Jiang jun Lu ba zi; Jiang jun Lu dang shen Jie geng Lu feng fang Jie sui Lu hui Jin geng Lu jiao jiao Jin qian cao Lu pi jiao Jin wen Lu rong Jin yin hua Luo han ye; Ju hua Luo shui chen Jun zi; Ma huang Kong sha shen Ma huang gen Ku ding xiang Mai dong Ku lian pi; Mai men dong Ku qin Man jing shi Ku shen Man jing zi; Kun bu; Mao hua Kun cao Mao zhu Lai fu zi; Mo yao Lan cao Ming tian ma; Lao sang zhi Mu dan pi; Lei wan Mu fang ji; Li lu; Mu bei zi; Li zhi he; Mu tong Lian fang Mu xiang Lian peng Nan wu wei zi; Lian qiao Nan xing Nao zi; Sang ji sheng Nei

*jin Sang piao xiao Nen qin Sang shen Ning shui shi Sang shen zi; Nui zi; Sang ye; Ou jie Sang zhi Pang da hui Sha ren Pao jiang Sha ren ke; Peng e zhu Sha yuan ji li; Peng zhu Shan dou gen Pi pa ye; Shan qi; Pian jiang huang Shan shen Pian qin Shan yao Po gu zhi Shan yu rou Pu huang Shan zhi zi; Qi ai; Shang lu; Qi lin jie Shen jiang Qi zi; Shen san qi; Quan cao Sheng di; Qian cao gen-Sheng di huang Qian dan Sheng jiang Qian hu; Sheng ma; Qiang huoeng Sheng shai shen Qin pi; Sheng tie luo Qin jiao Shi gao Qing hao Shi liu hiang Qing pi; Shi zhi cao Qiu chai hu; Shou wu; Qu mai Shi di; Quan chong Shu di huang Quan dang gui Shu jiao Quan gua lou Shu jin teng Quan xie Shuang hua Ren dong ha; Shuang sang ye; Ren shen Su he xiang Ren shen lu; Suan zao ren Ren shen ye; Tai zi shen Rou cong rong Tang shen Rou dou kou Tao ren Rou gui Tian dong Ruan chai hu; Tian gua di; San qi; Tian ma; San qi hua Tian ma jiao Sang bai pi; Tian men dong Sang gen bai pi; Tian qi; Sang ji; Tiao qin Tu fu ling, Xing tou cao, Tong shen, Xiong dan, Tong ji li; Xiong qiong Tu gou qi; Xu duan Tu niu xi; Xuan hu; Tu si; Xuan hu suo Tuo li cao Xuan shen Wa leng Xue dan shen Wa long zi; Xue jie Wei gen Xue po; Wei jing Ya dan zi; Wei lian Ya lian Wei ling xian Yan hu; Wen zhu Yan hu suo Wu bei zi; Yang huo Wu gong Ye jiao teng Wu hua long gu; Ye ju; Wu ling zhi Ye ju hua Wu mei Yi ren Wu tou Yi yi ren Wi wei zi; Yi zhi ren Wu yue ai; Yin chai hu; Wu zei gu; Yin chen hao Xi chai hu; Yin er; Xi gua Yin guo ye; Xi hong hua Yin hu; Xi huang Yin hua Xi jiao Yin xing Xi xiang ru; Yin yang huo Xi xin Yin yang lian Xi yang shen Ying chai hu; Xia ku cao Ying chun hua Xian he cao Yu bai fu; Xian ling pi; Yu guo Xian mao Yu jin Xiang bai zhi Yu li ren Xiang bei Yu zhu Xiang chi Yuan cun xiang Xiang gao ben Yuan hu; Xiang gua di; Yuan shen Xiao hui Yuan wei ban Xie ye; Yuan wu ban Xie bai Yuan zhi Xin yi; Yue yue hong Xin yi hua Yun lian Xing ren Yun ling Zang hong hua Zao jiao, Zao pi; Ze lan Ze qi; Ze xie Zhang nao Zhe bei Zhe bei mu; Zhe chong Zhe shi Zhen zhu Zhi ke; Zhi mu; Zhi mu rou Zhi nan xing Zhi zi; Zhuer qing Zhu huang Zhu li; Zhu ling Zhu sha Zhu ye; Zhu you Zi bei fu ping Zi bei tian kui Zi cao Zi cao gen Zi dan shen Zi di ding Zi mu tong Zi ran tong Zi su ye; Zi su zi; Zi wan Zi zhu Zi zhu cao Zong lu pi.*

Additional herbs include, but are not limited to, herbs such as *Ashwagandha, Artemisia* sp., *Angelica* sp., Burdock root (*Arctium lappa*), Blessed thistle (*Cerbenia benedicta*), Bromelain, *Boswellia serrata, Cameliaaia sinensis*, Cayenne (*Capsicum anuum*), Cat's claw, Chapareal (*Larrea divaricata*), *Cinchona* sp., Comfrey (*Symphytum officinale*), Dalmation (Sage sp), Dandelion (*Taraxacum* sp.), Devil's claw (*Harpagophytum procumbens*), *Echinacea angustifolia*, Eluthero, *Eucalyptus globulus, Euphrasia*, Eyebright (*Euphrasia officinalis*), Fennel (*Foeniculum vulgare*), Fenugreek (*Trigonella foenumgraecum*), Feverfew (*Pyrethrum parthenium*), Frankincense, Gentian root (*Gentiana lutea*), Ginger (*Zingiberis officinalis*), Ginko leaf/root, Goldenseal (*Hydrastis Canadensis*), Gotu kola (*Centella asiatica*), Guggal (*Commiphora mukul*), Horehound (*Marrubium vulgare*), Hyssop (*Hyssopus officinalis*), Kava kava (*Piper methysticum*), Licorice root (*Glycyrrhiza* sp.), *Lobelia inflata*, Meadowsweet (*Filipendula ulmaria*), Mughal garam, Mullein (*Verbascum tapsus*), Myrrh (*Commiphora nayrrha*), Nettle (*Urtica urens*), Partridge berry (*Mitchella repens*), Pennyroyal (*Mentha pulegium*), Periwinkle, Plantain (*Plantago psyllium*), psyllium, *Pueraria* flower, *Rehmannia* root, Rosemary (*Rosarinus officinalis*), *Silybum* sp. (Milk thistle), *Scuttelaria* (Skullcap), Slippery elm (*Ulmus fulva*), St. john's wort (*Hypericum perforatum*), Tumeric, Uva ursi (*Arctostaphylos* sp), Valerian (*Valerian* sp.), Wild yam root (*Dioscorea villosa*), Yarrow (*Achillea millefolium*), Yellowdock (*Rumex crispus*)

Additionally, the designer of the product can use vitamins, antimicrobial agents, anti-inflammatory agents, non-steroidal cosmetic soothing agents, skin lightening agents, anti-wrinkle agents, anti-itching agents, antioxidants, fragrances, conditioners, and other agents or any combination thereof. Those skilled in the art will readily appreciate that substances other than those listed in the non-limiting examples below may also be employed.

Non-limiting examples of useful vitamins include, but are not limited to, vitamin A, vitamin $B_1$-$B_{12}$, biotin, vitamin C, pantothenic acid, vitamin K, vitamin D, vitamin E and mixtures thereof. Non-limiting examples of useful antimicrobial agents include, but are not limited to, beta-lactam drugs, quinolone drugs, ciprofloxacin, norfloxacin, tetracycline, erythromycin, amikacin, 2,4,4'-trichloro-2'-hydroxy diphenyl ether, 3,4,4'-trichlorobanilide, phenoxyethanol, phenoxy propanol, phenoxyisopropanol, doxycycline, capreomycin, chlorhexidine, chlortetracycline, oxytetracycline, clindamycin, ethambutol, hexamidine isethionate, metronidazole, pentamidine, gentamicin, kanamycin, ketoconazole, lineomycin, methacycline, methenamine, minocycline, neomycin, netilmicin, paromomycin, streptomycin, tobramycin, miconazole, tetracycline hydrochloride, erythromycin, zinc erythromycin, erythromycin estolate, erythromycin stearate, amikacin sulfate, doxycycline hydrochloride, capreomycin sulfate, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, amanfadine hydrochloride, amanfadine sulfate, octopirox, parachlorometa xylenol, nystatin, tolnaftate, zinc pyrithione; clotrimazole; alantolactone; isoalantolactone; alkanet extract (alaninin); anise; arnica extract (helenalin acetate and 11, 13 dihydrohelenalin); Aspidium extract (phloro, lucinol containing extract); barberry extract (berberine chloride); bay sweet extract; bayberry bark extract (myricitrin); benzalkonium chloride; benzethonium chloride; benzoic acid and its salts; benzoin; benzyl alcohol; blessed thistle; bletilla tuber; bloodroot; bois de rose oil; burdock; butyl paraben; cade oil; CAE (available from Ajinomoto, located in Teaneck, N.J.); cajeput oil; Cang-zhu; *capsicum frutescens* extract; caraway oil; cascarilla bark (sold under the tradename ESSENTIAL OIL); cedarleaf oil; chamomille; chaparral; chlorhexidine gluconate; chlorophenesin; chlorxylenol; cinnamon oil; citronella oil; clove oil; Crinipan AD (available from Climbazole); 2,3-dihydrofarnesol; dehydroacetic acid and its salts; dill seed oil; DOWICIL 200 (available from Dow Chemical, located in Midland, Mich.); echinacea; elenolic acid; epimedium; ethyl paraben; Fo-Ti; galbanum; garden bumet; GERMALL 115 and GERMALL II (available from ISP-Sutton Labs, located in Wayne, N.J.); German chamomile oil; giant knotweed; GLYDANT (available from Lonza, located in Fairlawn, N.J.); GLYDANT PLUS (available from Lonza); grapefruit seed oil; 1,6 hexanediol; hexamidine diisethionate; hinokitiol; honey; honeysuckle flower; hops; immortelle; iodopropynl butyl carbamide (available from Lonza); isobutyl paraben; isopropyl paraben; JM ACTICARE (available from Microbial Systems International, located in Nottingham, NG); juniper berries; KATHON CG (available from Rohm and Haas, located in Philadelphia, Pa.); kojic acid; labdanum; lavender; lemon balm oil; lemon grass; methyl paraben; mint; mume;

mustard; myrrh; neem seed oil; ortho phenyl phenol; olive leaf extract (available from Bio Botanica); parsley; patchouly oil; peony root; 1,2 pentandiol; PHENONIP (available from Nipa Labs, located in Wilmington, Del.); phenoxyethanol; phytosphingosine; pine needle oil; PLANSERVATIVE (available from Campo Research); propyl paraben; purslane; quillaira; rhubarb; rose geranium oil; rosemary; sage; salicylic acid; sassafras; savory; sichuan lovage; sodium meta bisulfite; sodium sulfite; SOPHOLIANCE (available from Soliance, located in Compiegne, France); sorbic acid and its salts; sphingosine; stevia; storax; sucrose esters; tarmic acid; tea; tea tree oil (cajeput oil); thyme; triclosan; triclocarban; tropolone; turpentine; umbelliferone (antifungal); yucca; and mixtures thereof.

Non-limiting examples of anti-inflammatory agents useful herein include, but are not limited to, hydrocortisone, non-steroidal anti-inflammatory agents such as oxicans, salicylates, acetic acid derivatives, fenamates, propionic acid derivatives, pyrazoles, substituted phenyl compounds, 2-naphthyl containing compounds, hydrocortisone, triamcinolone acetonide and natural anti-inflammatory agents such as *aloe* vera. Examples of anti-inflammatory agents are described in U.S. Pat. No. 5,487,884, the entire content of which is incorporated herein by reference. A preferred anti-inflammatory agent used in the practice of the invention is triamcinolone acetonide.

Non-limiting examples of useful cosmetic soothing agents include, but are not limited to, acetyl salicylic acid, ibuprofen, naproxen, benoxaprofen, flurbiprofen, fenoprofen, fenbufen, ketoprofen, indoprofen, pirprofen, carprofen, oxaprozin, pranoprofen, miroprofen, tioxaprofen, suprofen, alminoprofen, tiaprofenic acid, fluprofen, bucloxic acid, absinthium, *acacia*, aescin, alder buckthorn extract, allantoin, *aloe*, APT (available from Centerchem), amica, *astragalus, astragalus* root extract, azulene, Baicalin SR 15 (available from Barnet Products Dist.), baikal skullcap, baizhu, balsam canada, bee pollen, BIOPHYTEX (available from Laboratories Serobiologiques), bisabolol, black cohosh, black cohosh extract blue cohosh, blue cohosh extract, boneset, borage, borage oil, bradykinin antagonists, bromelain, *calendula, calendula* extract, Canadian Willowbark Extract (available from Fytokem), candelilla wax, Cangzhu, canola phytosterols, *capsicum*, carboxypeptidase, celery seed, celery stem extract, CENTAURIUM (available from Sederma), centaury extract, chamazulene, chamomile, chamomile extract, chaparral, chaste tree, chaste tree extract, chickweed, chicory root, chicory root extract, chirata, chishao, collodial oatmeal, comfrey, comfrey extract, CROMOIST CM GLUCAN (available from Croda), darutoside, dehurian angelica, devil's claw, divalent metals (such as, magnesium, strontium, and manganese), doggrass, dogwood, Eashave (available from Pentapharm), eleuthero, ELHIBIN (available from Pentapharm), ENTELINE 2 (available from Secma), ephedra, epimedium, esculoside; ethacrynic acid, evening primrose, eyebright, Extract LE-100 (available from Sino Lion), Fangfeng, feverfew, ficin, forsythia fruit, Fytosterol 85 (available from Fytokem), *ganoderma*, gaoben, Gatuline A (available from Gattefosse), gentian, germanium extract, gingko bilboa extract, ginkgo, ginseng extract, goldenseal, gorgonian extract, gotu kola, grape fruit extract, guaiac wood oil, guggal extract, helenalin esters, henna, honeysuckle flower, horehound extract, horsechestnut, horsetail, huzhang, *hypericum*, ichthyol, immortelle, ipecac, job's tears, jujube, kola extract, LANACHRYS 28 (available from Lana Tech), lemon oil, lianqiao, licorice root, ligusticum, *ligustrum*, lovage root, *luffa*, mace, magnolia flower, manjistha extract, margaspidin, matricin, melatonin, MICROAT IRC (available from Nurture), mints, mistletoe, Modulene (available from Seporga), mono or diglucosides of glabridin, mono or diglucosides of gentisin, MTA (5'-deoxy-5'-methylhioadenosine), mung bean extract, musk, N-methyl arginine, oat beta glucan, oat extract, orange, panthenol, papain, phenoxyacetic acid, peony bark, peony root, Phytoplenolin (available from Bio Botanica), phytosphingosine, Preregen (available from Pentapharm), purslane, QUENCH T (available from Centerchem), quillaia, red sage, rehmannia, rhubarb, rosemary, rosmarinic acid, royal jelly, rue, rutin, sandlewood, sanqi, sarsaparilla, saw palmetto, SENSILINE (available from Silab), SIEGESBECKIA (available from Sederma), stearyl glycyrrhetinate, Stimutex (available from Pentapharm), storax, strontium nitrate, sweet birch oil, sweet woodruff, tagetes, tea extract, thyme extract, tienchi ginseng, tocopherol, tocopheryl acetate, triclosan, turmeric, urimei, ursolic acid, white pine bark, witch hazel xinyi, yarrow, yeast extract, yucca, and mixtures thereof.

Non-limiting examples of anti-itch ingredients useful herein include, but are not limited to, Stimu-tex (available from Pentapharm); Takanal (available from Ikeda-Distributer); Ichthyol (available from International Sourcing-Distributor); Oxygenated Glyceryl Triesters (available from Seporgia); hydrocortisone; Pramoxine and mixtures thereof.

Non-limiting example of antioxidants useful herein include, but are not limited to, vitamin E, tocopheryl acetate, betaglucan, coenzyme Q10, butylated hydroxy toluene (BHT), butylated hydroxy anisole BHA, superoxide dismutose, propylgallate, and the like.

Non-limiting examples of useful skin conditioners include, but are not limited to, mineral oil, petrolatum, vegetable oils (such as soybean or maleated soybean oil), dimethicone, dimethicone copolyol, cationic monomers and polymers (such as guar hydroxypropyl trimonium chloride and distearyl dimethyl ammonium chloride) as well as combinations thereof. Illustrative moisturizers are polyols such as sorbitol, glycerin, propylene glycol, ethylene glycol, polyethylene glycol, polypropylene glycol, 1,3-butane diol, hexylene glycol, isoprene glycol, xylitol, fructose and mixtures thereof.

Kits:

In another aspect, a kit for treating skin conditions is provided. According to one embodiment, the invention comprises a container containing a composition comprising *calendula*, tea tree oil, *eucalyptus* oil, grape seed oil, and *aloe vera*. A person skilled in the art will be able to select a container based on the form of the composition and its intended use. For example, an aerosol spray may be supplied in a pressurized can, whereas a lotion may be provided in a plastic bottle. In some embodiments of the kit, an applicator, such as a gauze, a cotton swab or a brush, may also be included.

In addition, a set of instructions is provided. The set of instructions preferably includes information necessary for proper use of the kit, such as dosage and timing of administration of the composition disclosed herein. The set of instruction may comprise instructions on treating skin diseases such as rashes, blisters, acne, fungal infections, burns, insect bites, microbial or infections, sunburn, scabies, scrapes, cuts surgical incisions, skin irritations, chapped lips, cracked skin and combinations thereof. A person of ordinary skill in the art will appreciate that the set of instructions can be in any suitable medium, including, without limitation, printed, video-taped, digital, and audio-recorded.

Methods for Treatment Skin Diseases:

The kit provides a practitioner with many of the tools necessary to treat skin affected by a skin disease. These methods comprise administering an effective amount of composition as described above to the effected skin. Skin diseases that can be treated by these methods include, but are not limited to, rashes, blisters, acne, fungal infections such as athlete's foot, ringworm, burns, insect bites, microbial infections, sunburn, scabies, scrapes, cuts, and combinations thereof.

The terms "treat", "treatment" or "treating" refer to executing a protocol, which may include administering one or more drugs to a patient (human or otherwise), in an effort to alleviate sighs or symptoms of the disease. Alleviation can occur prior to signs or symptoms of disease appearing, as well as after their appearance. Thus, "treat", "treating" or "treatment" includes "prevent", "preventing" or "prevention" of the disease. In addition, "treat", "treating" or "treatment" does not require complete alleviation of signs or symptoms, does not require a cure, and specifically includes protocols which have only a marginal effect on the patient.

The term "effective amount" means a quantity of an agent which, when administered to a patient or subject, is sufficient to result in an improvement in patient's condition. The improvement maybe determined in a variety of ways. Additionally, the improvement does not mean a cure and may include only a marginal change in patient's condition.

A person with ordinary skill in the art will undoubtedly be capable of determining the effective amount of the composition needed for a particular treatment. Such amount may depend on the strength of the composition or extent of the disease. Although a person with ordinary skill in he art will know how to select a treatment regimen for a specific condition, preferably, the composition may be applied 2 to 3 times a day or 3 to 4 times a day. It is foreseeable in some embodiments that the composition is administered over a period of time. The composition may be applied for a day, multiple days, a week, multiple weeks, a month, or even multiple months in severe circumstances. Alternatively, the composition may be applied only once when the skin condition is mild.

EXAMPLES

Example 1

"Dublin"; a 11 yr Old, Male, Neutered, Doberman

Anal mass (hepatoid/perianal) adenoma approximately 3 cm.×2 cm was removed. Composition was applied to incision 2-3 times a day. 4 days post-op incision looked great. Inflammation and swelling completely resolved. Dog has not attempted to bite or lick at incision site due to the salves ability to decrease the irritation, inflammation and swelling that usually comes along with the healing of a surgical incision. 3 week post-op exam showed complete resolution of incision site and the beginnings of hair regrowth. At no time did this dog attempt to pull out stitches from the surgical site.

Example 2

"Minx"; a 1½ yr Old Domestic Short Haired (DSH) Cat, Male, Neutered

Presented with right forelimb lameness of 2 weeks duration. Swelling developed, according to the owner, four days after the lameness started. Minx was constantly licked at this paw. He was taken to the local veterinarian who put him on antibiotics and placed an e-collar on him to prevent him from touching the leg. After examination at hospital, it was noted that an insect bite or spider bite was the cause of the problem. Composition was prescribed topically 2-3 times a day. Twenty-four hours after treatment started the swelling and inflammation was resolved. The owner said, "It's like a miracle, the swelling is down, overnight the paw was better". There was no need for the e-collar at any time.

Example 3

"Ares," a 3 yr Old Male, Intact, Portuguese Waterdog

Dog was in a fight with another dog that resulted in a 4 cm long wound on the leg. The wound required debridement under anesthesia. Applying the composition topically 3-4 times a day for the next 7 days resulted in a completely healed area without any evidence of infection, odor, swelling or inflammation at any time.

Example 4

"Zoe"; a 7 yr old, Female, Intact, DSH (Domestic Short Haired) Feline

Presented with a puncture wound of unknown origin located along the caudal dorsum at the midline level. The surrounding tissue was injured as noted by the purple, black & blue discoloration. Composition was applied topically 2-3 times a day. As a result of this patient being hospitalized due to the placement of a ¼ inch Penrose drain, assessment of the wound was possible on a daily basis. Observations showed that within 24 hrs the skin bruising and discoloration was improving significantly. Skin swelling was decreased and discharge from the puncture had stopped. Within 72 hours the drain was pulled and the swelling and inflammation was approximately 75% reduced. At no time did "Zoe" attempt to remove the drain or interfere with the healing process.

Example 5

"Kuma"; a 13 yr Old, Male, Neutered, Akita

Presented with chronic "hot spots" (acute moist dermatitis) of many years duration. Severely swollen, irritated and inflamed digits and paws were present with a deep pyoderma (deep skin infection) of all the paws and digits. All paws were extremely red, weeping with a strong odor. The owners were told to apply the composition topically a minimum of four times a day, noting that the more contact time on the effected skin the better the response. This situation had been going on a number of years and was chronic and quite severe.

Example 6

"George"; a 11 yr Old, Male, Neutered, DSH

Presented with a distribution of pustules and scabs under his ventral chin of 6 months duration. He was diagnosed with Feline Acne. Treatment involved topical application of the composition liberally to the effected areas 2-4 times a day. The entire area was healed at the re-examination 10 days later. The owner commented that George did not scratch or rub the area during the treatment period.

Example 7

"Sasha"; a 9 yr Old, Male, Neutered, Yorkshire Terrier

Presented with severe puriritis (itching) and generalized hair loss as a result of allergic skin disease. The skin between the digits had numerous superficial abrasions and ulcerations. Serum was oozing from the nail beds indicating possible bacterial or fungal infection. The composition was applied liberally and topically to all the effected areas of skin 2-3 times a day. Within 4 days the inflammation was significantly improved and the ulcerations were 80% healed.

Example 8

"Bunkers"; a 8 yr Old, Male, Neutered, Dalmatian

Presented with a raised, inflamed, swollen skin lesion that resulted from an engorged brown dog tick that was attached to the skin. The tick was removed but the mouths parts of the tick were embedded in the skin. These were subsequently excised. The composition was applied topically 2-4 times a day. The swelling and inflammation resolved completely by day 2. The dog did not attempted to remove the composition or lick it off indicating that pain, discomfort or itching were not present.

Example 9

"Catie"; a 7 yr Old, Female, Spayed, Collie

Presented with a laceration of the front medial pad and surrounding tissues. Composition was applied topically 2-4 times a day and resolved within a week. No infection, swelling or inflammation developed. Owner was able to apply composition easily to area.

Example 10

"Jax"; a 5 yr Old, Male, Intact, Ferret

Presented with superficial abrasions and ulcerations of the inguinal areas as a result of urine scald. This was the result of the acidic nature of urine and its ability to burn the skin if not washed off and treated. The patient was treated 3 times a day for 1 week and entire skin regrowth occurred. The composition could potentially have a similar effect with human burn victims.

Example 11

"Tootsie"; a 8 Months Old, Female, Spayed, Beagle

Presented because of a self-inflicted wound that resulted from constant licking at her front paw. There are various medical and non-medical reasons why a pet might do this, however, the result in this case was ulceration and subsequent infection of the skin between the toes (interdigital dermatitis). Salve was applied 3-4 times a day and complete resolution occurred within 5 days.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A method of treating skin affected by a skin disease in a mammal comprising:
   identifying a subject having an area of skin affected by a skin disease selected from the group consisting of rash, blister, fungal infection, burn, bacterial infection, insect bite, microbial infection, sunburn, scrape, cut, surgical incision, skin irritation, chapped lips, cracked skin, dermatitis and combinations thereof; and
   administering to the affected area of the patient's skin an effective amount of a composition consisting of 20% to about 65% weight per volume of *Calendula* Oil, from about 0.01% to about 5% weight per volume of Tea Tree Oil, from about 0.01% to about 15% weight per volume of *Eucalyptus* Oil, from about 0.01% to about 15% weight per volume of Grape Seed Oil, and from about 0.01% to about 20% weight per volume of *Aloe Vera* Oil, from about 0.01 to 8% weight per volume of Vitamin E, from about 0.00 to 20% weight per volume of Shea Butter, from about 0.01% to about 2% of weight per volume Rosemary oil, from about 0.00% to about 40% weight per volume of beeswax, from about 15% to about 55% weight per volume of vegetable oil and from about 0.00% to about 40% weight per volume of herbs.

2. The method of claim 1, wherein the skin disease is fungal infection, bacterial infection, microbial infection or a combination thereof.

3. A method of treating skin affected by a skin disease in a mammal comprising:
   identifying a subject having an area of skin affected by a skin disease selected from the group consisting of rash, blister, fungal infection, burn, bacterial infection, insect bite, microbial infection, sunburn, scrape, cut, surgical incision, skin irritation, chapped lips, cracked skin, dermatitis and combinations thereof; and administering to the affected area of the patient's skin an effective amount of a composition consisting of 20% to about 65% weight per volume of *Calendula* Oil, from about 0.01% to about 5% weight per volume of Tea Tree Oil, from about 0.01% to about 15% weight per volume of *Eucalyptus* Oil, from about 0.01% to about 15% weight per volume of Grape Seed Oil, and from about 0.01% to about 20% weight per volume of *Aloe Vera* Oil, from about 0.01 to 8% weight per volume of Vitamin E, from about 0.00 to 20% weight per volume of Shea Butter, from about 0.01% to about 2% of weight per volume Rosemary oil, from about 0.00% to about 40% weight per volume of beeswax, from about 15% to about 55% weight per volume of vegetable oil, from about 0.00% to about 40% weight per volume of herbs, water, and an emulsifier.

4. The method of claim 3, wherein the composition is in a form of water-in-oil or oil-in-water emulsion.

* * * * *